United States Patent
Yao et al.

(10) Patent No.: US 9,962,378 B2
(45) Date of Patent: May 8, 2018

(54) ROS1 INHIBITOR AND ITS USE

(71) Applicant: Macau University of Science and Technology, Taipa, Macau (CN)

(72) Inventors: Xiao Jun Yao, Taipa (CN); Lai Han Leung, Taipa (CN); Lian Xiang Luo, Taipa (CN); Liang Liu, Taipa (CN)

(73) Assignee: Macau University of Science and Technology, Taipa (MO)

( * ) Notice: Subject to any disclaimer, the term of this patent is extended or adjusted under 35 U.S.C. 154(b) by 0 days. days.

(21) Appl. No.: 14/927,825

(22) Filed: Oct. 30, 2015

(65) Prior Publication Data
US 2017/0079972 A1    Mar. 23, 2017

Related U.S. Application Data

(60) Provisional application No. 62/219,724, filed on Sep. 17, 2015.

(51) Int. Cl.
*A61K 31/4743*    (2006.01)

(52) U.S. Cl.
CPC ................................. *A61K 31/4743* (2013.01)

(58) Field of Classification Search
CPC combination set(s) only.
See application file for complete search history.

(56) References Cited

U.S. PATENT DOCUMENTS

| | | | | |
|---|---|---|---|---|
| 8,426,437 B2 * | 4/2013 | Bienayme | ............ | C07D 471/04 514/290 |
| 8,642,660 B2 * | 2/2014 | Goldfarb | ............... | A61K 31/122 514/18.9 |
| 2009/0163545 A1 * | 6/2009 | Goldfarb | ............... | A61K 31/122 514/312 |

FOREIGN PATENT DOCUMENTS

| | | | | |
|---|---|---|---|---|
| WO | WO 2007003611 A1 * | 1/2007 | ........... | C07D 471/04 |
| WO | WO 2009107850 A2 * | 9/2009 | ........... | C07D 471/04 |

OTHER PUBLICATIONS

N. Cancer Genome Atlas Research, "Comprehensive molecular profiling of lung adenocarcinoma," Nature, vol. 511, No. 7511, pp. 543-550, 2014.

K.D. Davies, A.T. Le, M.F. Theodoro, et al., "Identifying and targeting ROS1 gene fusions in non-small cell lung cancer," Clin Cancer Res, vol. 18, No. 17, pp. 4570-4579, 2012.
K.D. Davies,and R.C. Doebele, "Molecular pathways: ROS1 fusion proteins in cancer," Clin Cancer Res, vol. 19, No. 15, pp. 4040-4045, 2013.
A.T. Shaw, S.H. Ou, Y.J. Bang, et al., "Crizotinib in ROS1-rearranged non-small-cell lung cancer," N Engl J Med, vol. 371, No. 21, pp. 1963-1971, 2014.
M.A. Davare, N.A. Vellore, J.P. Wagner, et al., "Structural insight into selectivity and resistance profiles of ROS1 tyrosine kinase inhibitors," Proceedings of the National Academy of Sciences, vol. No. pp. 201515281, 2015.
H.J. Lee, G. Zhuang, Y. Cao, et al., "Drug resistance via feedback activation of Stat3 in oncogene-addicted cancer cells," Cancer Cell, vol. 26, No. 2, pp. 207-221, 2014.
C.M. Lovly, and A.T. Shaw, "Molecular pathways: resistance to kinase inhibitors and implications for therapeutic strategies," Clin Cancer Res, vol. 20, No. 9, pp. 2249-2256, 2014.
K. Rikova, A. Guo, Q. Zeng, et al., "Global survey of phosphotyrosine signaling identifies oncogenic kinases in lung cancer," Cell, vol. 131, No. 6, pp. 1190-1203, 2007.
H.Y. Zou, L. Friboulet, D.P. Kodack, et al., "PF-06463922, an ALK/ROS1 Inhibitor, Overcomes Resistance to First and Second Generation ALK Inhibitors in Preclinical Models," Cancer Cell, vol. 28, No. 1, pp. 70-81, 2015.
M.A. Davare, A. Saborowski, C.A. Eide, et al., "Foretinib is a potent inhibitor of oncogenic ROS1 fusion proteins," Proc Natl Acad Sci U S A, vol. 110, No. 48, pp. 19519-19524, 2013.

* cited by examiner

*Primary Examiner* — Kamal Saeed
(74) *Attorney, Agent, or Firm* — Renner Kenner Greive Bobak Taylor & Weber (57) ABSTRACT

The administration of a compound advantageously efficacious as ROS1 inhibitor and its effect on subjects with cancer includes administering a compound having certain structural components such as a quinoline moiety in the backbone and at least one tertiary amine containing moiety in a side chain as well as heteroatoms, in particular oxygen atoms, present in the backbone and the side chain for treating a subject suffering from a disease such as cancer. The presence of such structural components allows for an advantageous interaction with the ROS1 kinase domain, in particular with the hinge region. The administered compounds represent a highly promising opportunity in particular for patients bearing ROS1-dependent cancer. A method for targeting tumor cells harboring an abnormality in ROS1 gene includes contacting a cell with compounds of the present invention as well as pharmaceutical compositions comprising such compounds.

17 Claims, 5 Drawing Sheets

ROS1 INHIBITOR AND ITS USE

CROSS-REFERENCE TO RELATED APPLICATIONS

The present application claims priority to U.S. Provisional Patent Application No. 62/219,724, filed Sep. 17, 2015, and incorporated herein by reference.

FIELD OF THE INVENTION

The present invention relates to the administration of a novel compound efficacious as ROS1 inhibitor and its effect on subjects with cancer. More specifically, the present invention is directed to a method for administering a compound having certain structural components for treating a subject suffering from a disease such as cancer, in particular ROS1-dependent non-small-cell lung cancer. The present invention further provides a method to target tumor cells harboring an abnormality in ROS1 gene as well as pharmaceutical compositions comprising said compound.

BACKGROUND OF THE INVENTION

Adenocarcinoma of the lung is the leading cause of cancer-related death worldwide. Recently, chromosomal rearrangements involving the c-ros oncogene 1 (ROS1) receptor tyrosine kinase (RTK) genes have been described in a variety of multiple human cancers, including non-small-cell lung cancer (NSCLC) (Cancer Genome Atlas Research, Nature, 2014, 511(7511):543-550). Such rearrangements are accompanied by the fusion of a portion of ROS1 that includes its entire tyrosine kinase domain with several partner proteins with resulting ROS1 fusion kinases being constitutively activated and driving cellular transformation (Shaw A. T. et al., N Engl J Med, 2014, 371(21):1963-1971). The kinase domain of ROS1 is known to become constitutively active while driving cellular proliferation along with such rearrangements (Davies K. D. and Doebele R. C., Clin Cancer Res, 2013, 19(15):4040-4045). ROS1 fusion kinases activate growth and survival pathways necessary for the growth and survival of cancer cells, which pathways are reported to include auto-phosphorylation of ROS1 and phosphorylation of AKT, ERK and STAT3 (Davies K. D. and Doebele R. C., Clin Cancer Res, 2013, 19(15):4040-4045). In this context, ROS1 rearrangement defines a distinct molecular subgroup of NSCLC. Rearrangement of genes encoding ROS1 is reported to occur in approximately 1%-2% of NSCLC cancers (Davies K. D. et al., Clin Cancer Res, 2012, 18(17):4570-4579; Davies K. D. and Doebele R. C., Clin Cancer Res, 2013, 19(15):4040-4045). Accordingly, of the estimated 1.5 million new cases of NSCLC worldwide each year, approximately 15,000 may be associated with and driven by oncogenic ROS1 fusions, especially to be found in NSCLC patients who are non-smoker or with light smoking history, of younger age and have histologic features of adenocarcinoma (Shaw A. T. et al., N Engl J Med, 2014, 371(21):1963-1971). The clinical success of targeting oncogenic tyrosine kinases has launched a new area of cancer therapy.

Crizotinib, which is a potent, ATP-competitive small molecule ALK inhibitor has also been used as a ROS1 inhibitor and is currently in clinical evaluation for lung cancer patients harboring ROS1 rearrangements. Although crizotinib shows promising early favorable response in patients with ROS1-rearranged NSCLC, its efficacy is more and more limited due to the development of drug resistance. Hence, ensuring durable response to crizotinib therapy represents an universal challenge as drug resistance proved to be common due to several resistance mechanism observed in patients treated with crizotinib including acquired point mutations, gene amplification and activation of alternative signaling pathways (Davare M. A. et al., Proceedings of the National Academy of Sciences, http://www.pnas.org/cgi/doi/10.1073/pnas. 1515281112; Lee H. J. et al., Cancer Cell, 2014, 26(2):207-221; Lovly C. M. and Shaw A. T., Clin Cancer Res, 2014, 20(9):2249-2256; Rikova K. et al., Cell, 2007, 131(6):1190-1203). Accordingly, patients who responded to crizotinib will eventually experience disease progression despite continued treatment.

Thus, identification of potent ROS1 inhibitors for cancer therapy is necessary (Zou H. Y. et al., Cancer Cell, 2015, 28(1): 70-81). Accordingly, there is a strong need for new compounds which are able to target ROS1 and sufficiently inhibit ROS1 kinase activity, which compounds can, thus, be used for cancer therapy, in particular for treatment of NSCLC.

SUMMARY OF THE INVENTION

The present invention provides in a first aspect a method for treating a subject suffering from a disease, in particular suffering from cancer. The method of the present invention comprises the step of administering an effective amount of a compound to the subject, in particular a mammal.

Said compound of the present invention has a structure of Formula (I):

Formula (I)

In Formula (I), ═══ represents a single or double bond. $X_1$, $X_2$ and $X_3$ are each independently selected from a N, S, O or C atom. $R^1$, $R^2$, $R^3$ and $R^4$ are each independently selected from hydrogen, halogen, $C_1$-$C_5$ haloalkyl, nitro, cyano, straight chain or branched $C_1$-$C_5$-alkyl and $R^5$ is selected from hydrogen, straight chain or branched $C_1$-$C_5$-alkyl or optionally substituted $C_7$-$C_{10}$-aralkyl. $R^6$, $R^7$ and $R^8$ are independent from each other absent or selected from hydrogen, straight chain or branched $C_1$-$C_5$-alkyl, optionally substituted $C_6$-$C_{10}$-aryl, optionally substituted $C_7$-$C_{10}$-aralkyl or a group of Formula (II):

Formula (II)

In Formula (II), both n and m are an integer, wherein n is selected from 0, 1, 2 or 3 and m is selected from 1, 2, 3 or 4, wherein the sum of n and m is at most 4. $R^9$ and $R^{10}$ in

Formula (II) are each independently selected from a straight chain or branched $C_1$-$C_5$-alkyl. At least one of $R^6$, $R^7$ and $R^8$ is a group of Formula (II).

Also contemplated by the present invention is the free base, any pharmaceutically acceptable salt or solvate or anhydrate of the compound of Formula (I).

Hence, the compound of the present invention comprises certain structural components, namely a quinoline moiety in the backbone, i.e. the core part of the compound, at least one a tertiary amine containing moiety in a side chain attached to the backbone and further heteroatoms, in particular oxygen atoms, in the backbone in form of a 2-oxo group, i.e. in 2-position in relation to the nitrogen atom of the quinoline, and one oxygen atom present in the at least one tertiary amine containing moiety in form of an amide moiety.

According to the invention is also the compound of Formula (I) for use as a medicament, preferably for use in the treatment of cancer such as NSCLC. Furthermore, the invention refers to the use of the compound of Formula (I) for preparing a medicament for treatment of a disease, in particular cancer such as NSCLC.

The present invention in another aspect refers to a method for targeting tumor cells harboring an abnormality in ROS1 gene, in particular resulting from a ROS1 chromosome rearrangement such as those associated with the expression of a ROS1 fusion kinase selected from SCL34A2-ROS1 or CD74-ROS1. Said method of the present invention comprises the step of contacting said cells with a compound of Formula (I) or a salt, solvate or anhydrate thereof:

Formula (I)

$X_1$ to $X_3$, $R^1$ to $R^{10}$ are as defined above, wherein at least one of $R^6$, $R^7$ and $R^8$ is a group of Formula (II) with n and m as defined above, too. ═══ represents a single or double bond.

In still another aspect, a pharmaceutical formulation comprising the compound of Formula (I) is provided. Said pharmaceutical composition comprises a compound of Formula (I) or a pharmaceutically acceptable salt, solvate or anhydrate thereof as active ingredient:

Formula (I)

$X_1$ to $X_3$, $R^1$ to $R^{10}$ are as defined above, wherein at least one of $R^6$, $R^7$ and $R^8$ is a group of Formula (II) with n and m as defined above, too. ═══ represents a single or double bond.

The pharmaceutical formulation further comprises physiologically tolerable excipients and may additionally contain further active ingredients, in particular therapeutic compounds for treating cancer such as NSCLC. The present invention also refers to the use of said pharmaceutical formulation for inhibiting ROS1 kinase activity, in particular ROS1 fusion kinase activity, such as for suppressing phosphorylation of ROS1 kinase, in particular ROS1 fusion kinase, and/or inhibiting the anti-apoptotic and growth signaling downstream to ROS1 kinase, in particular ROS1 fusion kinase.

Other features and aspects of the invention will become apparent by consideration of the following detailed description and accompanying drawings.

DETAILED DESCRIPTION OF ILLUSTRATIVE EMBODIMENTS

The present invention in a first aspect refers to a method for treating a subject suffering from a disease. Said disease is preferably cancer, in particular a ROS1-dependent cancer.

The term "ROS1-dependent" as used within this patent application refers to a cancer with tumor cells harboring an abnormality in ROS1 gene. Said abnormality in ROS1 gene preferably results from a ROS1 chromosome rearrangement, also referenced as ROS1 gene fusion. Hence, preferably, ROS1-dependent means cancer with tumor cells harboring an abnormality in ROS1 gene, which abnormality in ROS1 gene results from a ROS1 chromosome rearrangement. Especially preferably, said ROS1 chromosome rearrangement is associated with the expression, preferably a detectable increase, of a ROS1 fusion kinase in particular selected from the group consisting of SCL34A2-ROS1, CD74-ROS1, CLTC-ROS1, EZR-ROS1, TPM3-ROS1, SDC4-ROS1, LRIG3-ROS1, KDELR2-ROS1, CCDC6-ROS1, LIMA1-ROS1 and MSN-ROS1, more preferably selected from the group consisting of SCL34A2-ROS1 and CD74-ROS1. In all these fusion kinases, the ROS1 kinase domain of ROS1 wild type kinase is fully retained. I.e. ROS1-dependent cancer or subjects preferably have a detectable expression, in particular an increased expression, of at least one ROS1 fusion kinase, respectively, as a result of the fusion between ROS1 gene and another gene.

ROS1 wild type kinase, its structure as well as ROS1 gene rearrangements and gene fusions, respectively, as well as resulting ROS1 fusion kinases are known to the skilled person (Davies, K. D., Clin Cancer Res, 2013, 19(15):4040-4045, Cancer Genome Atlas Research Network, Nature, 511:543-550 and Davies M. D. and Doebele R. C., Clin Canc Res, 2013, 19(15):4040-4045).

"ROS1 wild type kinase" (or -protein) generally refers to the respective full length protein with the sequence as encoded in normal (healthy) cells or tissue, namely non-cancerous cells or tissue, i.e. without ROS1 involving chromosome rearrangement. In contrast, "ROS1 fusion kinase" refers to the fusion protein expressed after ROS1 involving chromosome rearrangement in which at least the kinase domain of the ROS1 wild type protein fused to all or a portion of another protein and polypeptide, respectively. For example, SCL34A2-ROS1 is a fusion of a portion of the SCL34A2 polypeptide with a portion of the ROS1 polypeptide based on a gene fusion of respective encoding polynucleotides.

Whether a cancer or a subject is ROS1-dependent can be confirmed by respective molecular biological methods, wherein several methods are known to the skilled person (e.g. Shaw A. T. et al., N Engl J Med., 2014, 371(21):1963-1971, Davies M. D. and Doebele R. C., Clin Canc Res, 2013, 19(15):4040-4045). Commonly used and suitable methods especially include fluorescence in situ hybridization (FISH), immunohistochemistry (IHC) and quantitative real-time reverse transcription-PCR (qRT-PCR) assays. I.e. "ROS1-dependent cancer" is in particular considered for being a cancer in which at least one of the methods selected from FISH, IHC or qRT-PCR assay reveal a rearrangement involving the ROS1 gene. The same is true with regard to the specific type of ROS1 rearrangement, for which methods, in particular fusion partner specific assays, are known to the skilled person, as well.

The cancer is preferably a lung cancer, in particular a ROS1-dependent lung cancer. Preferably, the lung cancer is NSCLC, in particular a ROS1-dependent NSCLC. In especially preferred embodiments of the present invention, the disease is NSCLC, in particular a ROS1-dependent NSCLC.

The method of the present invention comprises a step of administering an effective amount of a compound or a pharmaceutically acceptable salt, solvate or anhydrate thereof to a subject. The subject is preferably a mammal, in particular a human. In preferred embodiments of the present invention, the subject is a mammal having an abnormality in ROS1 gene resulting from ROS1 chromosome rearrangement, which preferably includes ROS1 chromosome rearrangement with the generation of SCL34A2-ROS1 or CD74-ROS1 fusion kinases.

Said compound administered in the method of the present invention has a structure of Formula (I):

Formula (I)

In Formula (I) ═══ represents a single or double bond. $X_1$, $X_2$ and $X_3$ are each independently selected from a N, S, O or C atom. The skilled person will understand that the location and presence of double bonds within the 5-membered ring in Formula (I) depends on the specific $X_1$, $X_2$ and $X_3$ atoms present, preferably said 5-membered ring is at least partially unsaturated or aromatic.

Preferably, $X_1$, $X_2$ and $X_3$ are each independently selected from a N, S or C atom. More preferably, at least one of $X_1$, $X_2$ and $X_3$ is selected from a N or S atom, in particular at least one of $X_1$, $X_2$ and $X_3$ is a S atom. In especially preferred embodiments, $X_2$ and $X_3$ are a C atom with $X_1$ being a S atom. In an alternative embodiment, $X_3$ is a C atom with $X_1$ and $X_2$ being a N atom.

$R^1$, $R^2$, $R^3$ and $R^4$ are each independently selected from hydrogen, halogen, $C_1$-$C_5$ haloalkyl, nitro, cyano, straight chain or branched $C_1$-$C_5$-alkyl. Preferably, $R^1$, $R^2$, $R^3$ and $R^4$ are each independently selected from hydrogen, halogen, $C_1$-$C_2$ haloalkyl, nitro or cyano, which groups are mainly electron-withdrawing groups or deactivating groups. Electron-withdrawing groups or deactivating groups are atoms or functional groups that withdraw electron density from neighboring atoms. More preferably, $R^1$, $R^2$, $R^3$ and $R^4$ are each independently selected from hydrogen, halogen or $C_1$-$C_2$ haloalkyl, still more preferably from hydrogen or halogen and especially preferably from hydrogen, Cl, Br or F, in particular from hydrogen and Cl.

In a preferred embodiment of the present invention, three of $R^1$ to $R^4$ are hydrogen and one of them is a halogen selected from Cl, Br or F. More preferably, three of $R^1$ to $R^4$ are hydrogen and one of them is Cl in said embodiment. In particular embodiments of the present invention, $R^1$, $R^2$ and $R^4$ are hydrogen and $R^3$ is a halogen selected from Cl, Br or F, especially preferably $R^3$ is Cl.

$R^5$ is selected from hydrogen, straight chain or branched $C_1$-$C_5$-alkyl or optionally substituted $C_7$-$C_{10}$-aralkyl. Preferably, $R^5$ is selected from hydrogen, straight chain or branched $C_1$-$C_5$-alkyl or $C_7$-$C_{10}$-aralkyl. More preferably, $R^5$ is selected from straight chain or branched $C_1$-$C_4$-alkyl. Still more preferably, $R^5$ is selected from methyl or ethyl. In particular embodiments, $R^5$ is methyl.

$R^6$, $R^7$ and $R^8$ are independent from each other absent or selected from hydrogen, straight chain or branched $C_1$-$C_5$-alkyl, optionally substituted $C_6$-$C_{10}$-aryl, optionally substituted $C_7$-$C_{10}$-aralkyl or a group of Formula (II):

Formula (II)

In Formula (II), n and m represent an integer. n is selected from 0, 1, 2 or 3 and m is selected from 1, 2, 3 or 4, wherein the sum of n and m is at most 4. Preferably, the sum of n and m, i.e. n+m, is at most 3 and in especially preferred embodiments at most 2, in particular n+m is 2. In preferred embodiments, n is selected from 0, 1 or 2 and m is selected from 1, 2 or 3, wherein n+m is preferably at most 3. More preferably, n is selected from 0 or 1 and m is selected from 1, 2 or 3, wherein n+m is preferably at most 3. In especially preferred embodiments, n is 0 and m is selected from 1, 2 or 3, in particular n is 0 and m is selected from 2 or 3, especially preferably n is 0 and m is 2.

At least one of $R^6$, $R^7$ and $R^8$ is a group of Formula (II) as described above.

Preferably, $R^6$, $R^7$ and $R^8$ are independent from each other absent or selected from hydrogen, straight chain or branched $C_1$-$C_5$-alkyl, $C_6$-$C_{10}$-aryl, $C_7$-$C_{10}$-aralkyl or a group of Formula (II). Still more preferably, $R^6$, $R^7$ and $R^8$ are independent from each other absent or selected from hydrogen, straight chain or branched $C_1$-$C_4$-alkyl, phenyl or a group of Formula (II). In especially preferred embodiments, at least one of $R^6$ or $R^7$ is a group of Formula (II) as described above; in particular $R^7$ is a group of Formula (II). In especially preferred embodiments of the present invention, $X_2$ and $X_3$ are a C atom with $X_1$ being a S atom and $R^7$ is a group of Formula (II) as described above with $R^8$ being absent and $R^6$ being hydrogen.

Preferably, $R^9$ and $R^{10}$ are independently selected from a straight chain or branched $C_1$-$C_5$-alkyl, preferably straight chain or branched $C_1$-$C_4$-alkyl. More preferably, $R^9$ and $R^{10}$ are independently selected from methyl, ethyl or straight chain or branched propyl, in particular from methyl or ethyl. In most preferred embodiments, $R^9$ and $R^{10}$ both are methyl, ethyl or straight chain propyl, in particular both are ethyl. The term "optionally substituted" as used herein means that said radical or group is either unsubstituted or substituted. "Substituted" means that one or more hydrogen atoms of that radical or group, preferably one to two hydrogen atoms, in particular one hydrogen atom, are replaced with certain substituents provided that the normal valency is not exceeded and that the substitution results in a chemically stable compound. For example, optionally substituted $C_7$-$C_{10}$-aralkyl means that the radial may be substituted or not. Use of the term $C_7$-$C_{10}$-aralkyl without the expression "optionally substituted" is to be understood to refer to unsubstituted $C_7$-$C_{10}$-aralkyl, only. This also applies with regard to the term "optionally substituted $C_6$-$C_{10}$-aryl" versus "$C_6$-$C_{10}$-aryl".

The term "$C_1$-$C_5$ alkyl" as a group used in the present invention refers to a hydrocarbyl radical comprising from 1 to 5 carbon atoms. Accordingly, "$C_1$-$C_4$ alkyl" refers to a hydrocarbyl radical comprising from 1 to 4 carbon atoms. The alkyl group can be linear, i.e. straight chain, or branched. "$C_1$-$C_5$ alkyl" includes all linear or branched alkyl groups with 1 to 5 carbon atoms, and thus includes methyl, ethyl, n-propyl, isopropyl, butyl and its isomers (e.g. n-butyl, isobutyl, sec-butyl and tert-butyl), pentyl and its isomers (n-pentyl, tert-pentyl neopentyl, isopentyl, sec-pentyl, 3-pentyl). The term "$C_7$-$C_{10}$ aralkyl" refers to an alkyl radical with an aryl ring, i.e. a radical having a formula -AB, wherein A is a branched or straight chain hydrocarbyl radical and B is an aryl ring, usually a phenyl ring, attached to the hydrocarbyl radical, both in total comprise from 7 to 10 carbon atoms. Examples of such groups include benzyl (i.e. phenylmethyl), phenethyl, phenylpropyl, phenylbutyl. The "$C_7$-$C_{10}$ aralkyl" is optionally substituted, i.e. at least one hydrogen atom, in particular one hydrogen atom, may be replaced with a substituent, for example, selected from a halogen, nitro, cyano, straight chain or branched $C_1$-$C_5$ alkyl, straight chain or branched $C_1$-$C_5$ alkoxy or the like. "$C_1$-$C_5$ alkoxy" refers to a radical having a formula -AB wherein A is an oxygen atom and B is a branched or straight chain $C_1$-$C_5$ alkyl, i.e. including, for example, methoxy, ethoxy, propyloxy, isopropyloxy, butyloxy and isobutyloxy.

"$C_6$-$C_{10}$ aryl" according to the invention means an aromatic hydrocarbon residue with 6 to 10 carbon atoms having an aromatic ring, and includes monocyclic and polycyclic hydrocarbons wherein the additional ring(s) of the polycyclic hydrocarbon may be aromatic or nonaromatic. The $C_6$-$C_{10}$ aryl is optionally substituted; i.e. it may contain further substituents, namely at least one hydrogen atom, in particular one hydrogen atom, is replaced with a substituent, for example, a halogen, nitro, cyano, straight chain or branched $C_1$-$C_5$ alkyl, straight chain or branched $C_1$-$C_5$ alkoxy or the like. Examples of "$C_6$-$C_{10}$ aryl" include phenyl, indenyl and naphthyl. The most preferred $C_6$-$C_{10}$ aryl is phenyl.

"Nitro" refers to a —$NO_2$ group, wherein "cyano" refers to a —CN group. The term "halogen" as a group or part of a group refers to fluoro (—F), chloro (—Cl), bromo (—Br), iodo (—I) unless otherwise indicated.

The term "$C_1$-$C_5$ haloalkyl" as used herein as a group refers to an alkyl group with 1 to 5 carbon atoms, wherein one or more hydrogen atoms are replaced with a halogen, in particular one hydrogen atom is substituted with a halogen. Examples of such groups include fluoroethyl, fluoromethyl, trifluoromethyl or trifluoroethyl and the like, in particular trifluoromethyl. I.e. "$C_1$-$C_2$ haloalkyl" refers to an alkyl group with 1 to 2 carbon atoms, wherein one or more hydrogen atoms are replaced with a halogen, in particular one hydrogen atom is substituted with a halogen.

As used herein, the term "solvate" refers to a complex of variable stoichiometry formed by a solute, i.e. compound of Formula (I), and a solvent. If the solvent is water, the solvate formed is a hydrate. As used herein, the term "anhydrate" means any compound free of the water of hydration, as would be understood in the art. Suitable pharmaceutically acceptable salts are those which are suitable to be administered to subjects, in particular mammals such as humans and can be prepared with sufficient purity and used to prepare a pharmaceutical formulation. Also contemplated by the present invention are any stereoisomers, tautomeric forms, enantiomers and racemates of the compound of Formula (I), which terms are known to the skilled person.

Said compound of Formula (I) is, amongst others, characterized by certain structural components, which were found to unexpectedly contribute to an advantageous inhibition of the activity of ROS1 receptor tyrosine kinase by interacting with amino acids within the ROS1 kinase domain and ROS1 binding pocket, respectively. Namely the compound of the present invention comprises a quinoline moiety in the backbone, at least one tertiary amine containing moiety in a side chain attached to said backbone and further heteroatoms in particular oxygen atoms present in the backbone, in particular in form of a 2-oxo function in the quinoline ring, and present in the at least one tertiary amine containing moiety in particular in form of an amide functional group. Further moieties which may be attached to the backbone or side chain according to Formula (I) do not impede the interaction of compound of Formula (I) with the ROS1 kinase domain and preferably allow for additional interactions including van der Waals forces and hydrogen bonds or hydrophobic interaction with the ROS1 kinase domain and, thus, further contribute to the exceptional interaction with ROS1.

The inventors unexpectedly found that the presence of these structural components allows for an advantageous interaction with the ROS1 tyrosine kinase domain, in particular with the hinge region. In particular, an advantageous and close interaction with the hinge region by formation of hydrogen bonds has been observed which is in particular attributed to the presence of a tertiary amine containing side chain allowing for an advantageous interaction with e.g. Asp2030, wherein said quinoline moiety and oxygen atoms present in the compound of Formula (I) ensure an exceptional interaction with, in particular, Met2029. Both interactions are considered for being important ones allowing for the advantageous interaction with the ROS1 kinase domain and a potent inhibition of the activity of ROS1 kinase and, hence, ROS1 fusion kinases as said ROS1 kinase domain is fully retained in known fusion partners, i.e. in known ROS1 fusion kinases. Additionally, hydrophobic interactions and optionally van der Waals forces due to the structure of compound of Formula (I) further contribute to the advantageous interaction with the ROS1 kinase domain.

Hence, a compound having a structure of Formula (I) represents a highly promising opportunity in particular for treatment of patients bearing ROS1-dependent cancer, as ROS1 kinases are required for the growth of tumor cells but not normal cells. I.e. the compound of the present invention can be used for inhibiting, reducing or preventing the proliferation of tumor cells or inducing apoptosis of tumor cells.

It is expected that the compound of Formula (I) binds to anaplastic lymphoma kinase (ALK, also known as ALK tyrosine kinase receptor) and respective fusion proteins, as well, as ALK and ROS1 kinase are reported to share 77% amino acid identity within the ATP binding site (Shaw A. T., N Engl J Med, 2014, 371(21):1963-1971) and to share more than 64% overall sequence homology in the kinase domain and about 84% within the ATP binding site (Davare, M. A. et al., PNAS, August 2015, www.pnas.org/cgi/doi/10.1073/pnas. 1515281112), respectively. Rearrangements of ALK gene were observed in several cancers including NSCLC while defining a distinct subgroup of NSCLC.

In a preferred embodiment of the present invention, the compound has a structure of Formula (I), wherein

$X_1$, $X_2$ and $X_3$ are each independently selected from a N, S or C atom;

$R^1$, $R^2$, $R^3$ and $R^4$ are each independently selected from hydrogen, halogen, $C_1$-$C_2$ haloalkyl, nitro or cyano;

$R^5$ is selected from straight chain or branched $C_1$-$C_4$-alkyl; and $R^6$, $R^7$ and $R^8$ are independent from each other absent or selected from hydrogen, straight chain or branched $C_1$-$C_4$-alkyl, optionally substituted phenyl or a group of Formula (II) with n and m being an integer, wherein n is selected from 0, 1 or 2 and m is selected from 1, 2 or 3 and wherein n+m is at most 3, and with $R^9$ and $R^{10}$ each being independently selected from a straight chain or branched $C_1$-$C_4$-alkyl, with the provisio that at least one of $R^6$, $R^7$ and $R^8$ is a group of Formula (II). More preferably, $R^6$, $R^7$ and $R^8$ are independent from each other absent or selected from hydrogen, straight chain or branched $C_1$-$C_4$-alkyl, phenyl or a group of Formula (II) in said embodiment, with the provisio that at least one of $R^6$, $R^7$ and $R^8$ is a group of Formula (II).

In preferred embodiments, the compound is a compound having Formula (III) or a pharmaceutically acceptable salt, solvate or anhydrate thereof and including any stereoisomers, tautomeric forms, enantiomers and racemates thereof:

Formula (III)

wherein $R^7$ is a group of Formula (II)

Formula (II)

with n=0 and m=2 and wherein $R^9$ and $R^{10}$ are independent from each other selected from methyl, ethyl or straight chain or branched propyl;

$R^5$ is selected from methyl or ethyl; and three of $R^1$ to $R^4$ are hydrogen and one of them is a halogen selected from Cl, Br or F, preferably selected from Cl.

Further preferably, the compound is a compound of Formula (III), wherein $R^7$ is a group of Formula (II)

Formula (II)

with n=0 and m=2 and wherein $R^9$ and $R^{10}$ are independent from each other selected from methyl or ethyl;

$R^5$ is selected from methyl or ethyl; and

$R^1$, $R^2$ and $R^4$ are hydrogen and $R^3$ is a halogen selected from Cl, Br or F, preferably from Cl.

In an especially preferred embodiment of the present invention, the compound is a compound having Formula (IV) or a pharmaceutically acceptable salt, solvate or anhydrate thereof and including any stereoisomers, tautomeric forms, enantiomers and racemates thereof:

Formula (IV)

In particular, the compound is the cationic form of compound of Formula (IV), i.e. a compound having Formula (V):

Formula (V)

As further shown below, respective data with HCC78 cell lines with ROS1 fusion gene further confirm that compound of Formula (V) is especially effective in inhibiting ROS1 kinase activity. The compound of Formula (V) proved to be highly cytotoxic and selective to cancer cells. It proved to advantageously target ROS1 fusion kinase while showing relatively low toxicity to normal lung cells. In particular, the compound of Formula (V) proved to exceptionally inhibit growth, induce apoptosis and suppress the phosphorylation of ROS1 fusion kinase while making use of the NSCLC cell line HCC78, which is a NSCLC cell line characterized by ROS1-driven activated signaling due to the presence of the SCL34A2-ROS1 fusion gene (Davare M. A. et al., Proc Natl Acad Sci USA, 2013, 110(48):19519-19524).

Hence, in an especially preferred embodiment of the present invention the method for treating a subject suffering from a disease, in particular cancer and especially ROS1-dependent cancer, in particular ROS1 dependent NSCLC, comprises administering an effective amount of a compound having Formula (IV) or (V) to a subject, in particular a mammal such as a human.

In embodiments of the present invention, the disease is ROS1-dependent NSCLC and the compound has an $IC_{50}$ on NSCLC cells of at most 10 μM and an $IC_{50}$ on normal lung cells being at least 2.5 times higher than the $IC_{50}$ on NSCLC cells.

In other embodiments of the present invention, the compound is a compound of Formula (IV) or (V) and the disease is ROS1-dependent NSCLC.

The effective amount of the compound of Formula (I) depends on the species, body weight, age and individual conditions and can be determined by standard procedures such as with cell cultures or experimental animals.

The method of the present invention may further include steps carried out before administering the compound of Formula (I) to the subject comprising:
Obtaining a sample, in particular tumor cells, from the subject;
Testing said sample for the level of ROS1 fusion kinase or identifying a ROS1 chromosome rearrangement;
Optionally correlating the level of ROS1 fusion kinase with outcome and if conditions are met, administrating the compound of Formula (I) to said subject.

According to the invention is also the compound of Formula (I), in particular the compound of Formula (IV) or (V), for use as a medicament, preferably for use in the treatment of cancer such as lung cancer, especially NSCLC, in particular ROS1-dependent cancer, especially ROS1-dependent NSCLC. The compound of Formula (I), in particular the compound of Formula (IV) or (V), can be used in an effective amount for treating a human. Another aspect of the invention refers to the use of the compound of Formula (I), in particular the compound of Formula (IV) or (V), for preparing a medicament for treatment of a disease, in particular of cancer, especially lung cancer, in particular NSCLC, especially ROS1-dependent NSCLC.

The compound of Formula (I) may be used in combination with other therapeutic compounds, preferably therapeutic compounds which are used for treating cancer such as lung cancer, especially NSCLC.

In another aspect of the present invention, the invention provides a method for targeting tumor cells harboring an abnormality in ROS1 gene. Said abnormality in ROS1 gene is preferably a ROS1 chromosome rearrangement. Preferably, the tumor cells express ROS1 fusion kinase, in particular selected from SCL34A2-ROS1 or CD74-ROS1 fusion kinase. The tumor cells are preferably from a lung tumor, more preferably from a NSCLC.

Said method comprises the step of contacting said cells with a compound of Formula (I) or a salt, solvate or anhydrate thereof:

Formula (I)

$X_1$ to $X_3$, $R^1$ to $R^{10}$ as well as n and m are as defined above including above referenced preferred embodiments of $X_1$ to $X_3$, $R^1$ to $R^{10}$ as well as n and m. ══ represents a single or double bond. Any stereoisomers, tautomeric forms, enantiomers and racemates of the compound of Formula (I) are contemplated by the present invention.

Especially preferably, the compound is a compound having Formula (III) or a salt, solvate or anhydrate thereof and including any stereoisomers, tautomeric forms, enantiomers and racemates thereof:

Formula (III)

wherein $R^7$ is a group of Formula (II)

Formula (II)

with n=0 and m=2 and wherein $R^9$ and $R^{10}$ are independent from each other selected from methyl, ethyl or straight chain or branched propyl;

$R^5$ is selected from methyl or ethyl; and three of $R^1$ to $R^4$ are hydrogen and one of them is a halogen selected from Cl, Br or F, preferably selected from Cl.

Further preferably, the compound is a compound of Formula (III), wherein $R^7$ is a group of Formula (II)

Formula (II)

with n=0 and m=2 and wherein $R^9$ and $R^{10}$ are independent from each other selected from methyl or ethyl;

$R^5$ is selected from methyl or ethyl; and

$R^1$, $R^2$ and $R^4$ are hydrogen and $R^3$ is a halogen selected from Cl, Br or F, preferably from Cl.

In a further preferred embodiment, the compound is a compound having Formula (IV) or a salt, solvate or anhydrate thereof and including any stereoisomers, tautomeric forms, enantiomers and racemates thereof:

Formula (IV)

In particular, the compound is the cationic form of compound of Formula (IV), i.e. a compound having Formula (V):

Formula (V)

Preferably, the proliferation of the tumor cells is inhibited, reduced or prevented or apoptosis of the tumor cells is induced.

Preferably, the tumor cells are contacted with the compound of Formula (I) for at least 12 h. The compound of Formula (I) is preferably used in a concentration of at least 2.5 µM, more preferably of at least 5 µM and especially preferably of at least 10 µM.

In especially preferred embodiments, the compound is a compound having Formula (IV) or (V)

Formula (IV)

-continued

Formula (V)

Formula (III)

wherein
R$^7$ is a group of Formula (II)

Formula (II)

with n=0 and m=2 and wherein R$^9$ and R$^{10}$ are independent from each other selected from methyl, ethyl or straight chain or branched propyl;
R$^5$ is selected from methyl or ethyl; and
three of R$^1$ to R$^4$ are hydrogen and one of them is a halogen selected from Cl, Br or F, preferably selected from Cl.

Further preferably, the compound is a compound of Formula (III),
wherein
R$^7$ is a group of Formula (II)

Formula (II)

with n=0 and m=2 and wherein R$^9$ and R$^{10}$ are independent from each other selected from methyl or ethyl;
R$^5$ is selected from methyl or ethyl; and
R$^1$, R$^2$ and R$^4$ are hydrogen and R$^3$ is a halogen selected from Cl, Br or F, preferably from Cl.

In a further preferred embodiment, the compound is a compound having Formula (IV) or a salt, solvate or anhydrate thereof and including any stereoisomers, tautomeric forms, enantiomers and racemates thereof:

Formula (IV)

wherein the concentration of compound (IV) or (V) is at least 5 μM, more preferably at least 10 μM.

In a further aspect, the invention provides a pharmaceutical composition comprising a compound of Formula (I) or a pharmaceutically acceptable salt, solvate or anhydrate thereof as active ingredient:

Formula (I)

X$_1$ to X$_3$, R$^1$ to R$^{10}$ as well as n and m are as defined above including above referenced preferred embodiments of X$_1$ to X$_3$, R$^1$ to R$^{10}$ as well as n and m. ═══ represents a single or double bond. Any stereoisomers, tautomeric forms, enantiomers and racemates of the compound of Formula (I) are contemplated by the present invention.

Said pharmaceutical composition further comprises physiologically tolerable excipients. The skilled person is able to select suitable excipients depending on the form of the pharmaceutical formulation and is aware of methods for manufacturing pharmaceutical formulations as well as able to select a suitable method for preparing the pharmaceutical formulation depending on the kind of excipients and the form of the pharmaceutical formulation.

The pharmaceutical formulation according to the invention can be present in solid, semisolid or liquid form to be administered by an oral, rectal, topical, parenteral or transdermal or inhalative route to a subject, preferably a human.

The pharmaceutical formulation may comprise further active ingredients, such as therapeutic compounds used for treating cancer, in particular lung cancer such as NSCLC.

Especially preferably, the compound is a compound having Formula (III) or a salt, solvate or anhydrate thereof and including any stereoisomers, tautomeric forms, enantiomers and racemates thereof:

In particular, the compound is the cationic form of compound of Formula (IV), i.e. a compound having Formula (V):

Formula (V)

The present invention also refers to the use of the pharmaceutical formulation of the present invention for inhibiting ROS1 kinase activity, in particular ROS1 fusion kinase activity, especially for suppressing phosphorylation of ROS1 kinase, in particular ROS1 fusion kinase, and/or inhibiting the anti-apoptotic and growth signaling downstream to ROS1 kinase, in particular ROS1 fusion kinase.

The skilled person is able to prepare the compound of Formula (I) with suitable purity and/or respective compounds are commercially available with sufficient purity.

The technical terms used in the present patent application have the meaning as commonly understood by a respective skilled person unless specifically defined.

The examples set out below further illustrate the invention. The preferred embodiments described above and the drawings as well as examples given below represent preferred or exemplary embodiments and a skilled person will understand that the reference to those embodiments or examples is not intended to be limiting.

EXAMPLES

HCC78 cells and CCD19-Lu cells were obtained from the American Type Culture Collection and cultured in environment of 5% $CO_2$ at 37° C. in RPMI-1640 (GIBCO, Lift Technologies) medium supplemented with 10% fetal bovine serum (FBS) (GIBCO, Lift Technologies), 100 units/mL penicillin, and 100 μg/mL streptomycin (GIBCO, Lift Technologies), crizotinib was purchased from Selleck Chemicals.

Descriptive analytical data in the examples below are presented as means±SEM. Statistical analysis was conducted using Graph Prim 5.0. One-way analysis of variance (ANOVA) was used to assess significant differences between datasets. Values of P<0.05 were considered statistically significant.

Example 1

Firstly, the binding mode between the compound of Formula (V) and ROS1 kinase has been determined.

In this context, molecular docking calculation has been performed to study the binding mode between the compound of Formula (V) and ROS1 kinase domain by using the Induced Fit Docking module in Schrodinger software. The 3D structure of the Compound of Formula (V) is prepared and optimized in the LigPrep module. The 3D structure of ROS1 kinase is derived from the PDB database (PDB ID: 3ZBF) and prepared using the Protein Preparation Wizard. The active site is defined by the centroid of crizotinib. The pose of ligand is evaluated with XP docking score. The pose with the highest score is selected for further analysis.

Figure 1A:
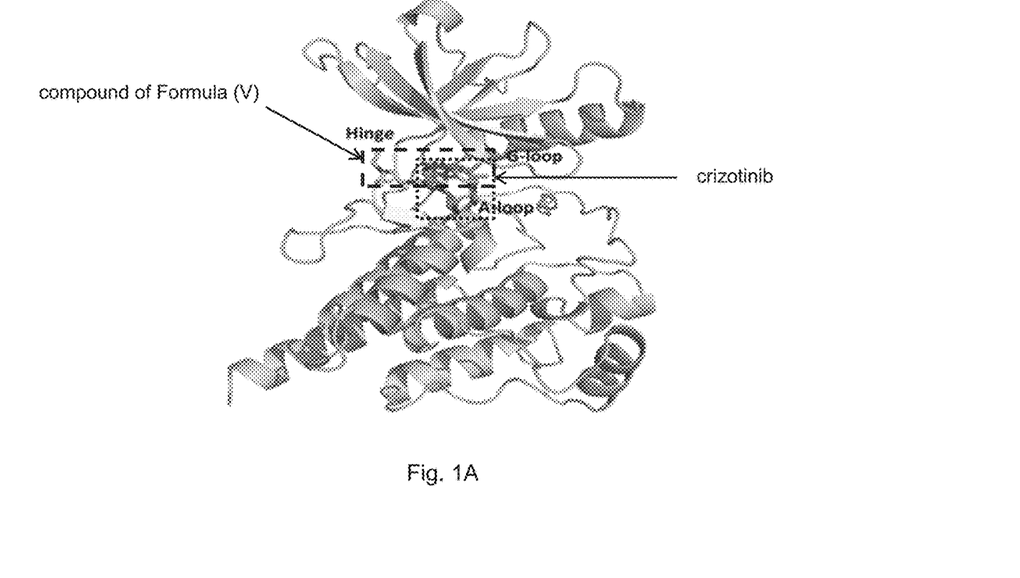
FIG. 1A shows 3D schematic representation of the structure of the compound of Formula (V), crizotinib and the binding pocket of the ROS1 kinase domain.
Figure 1B:
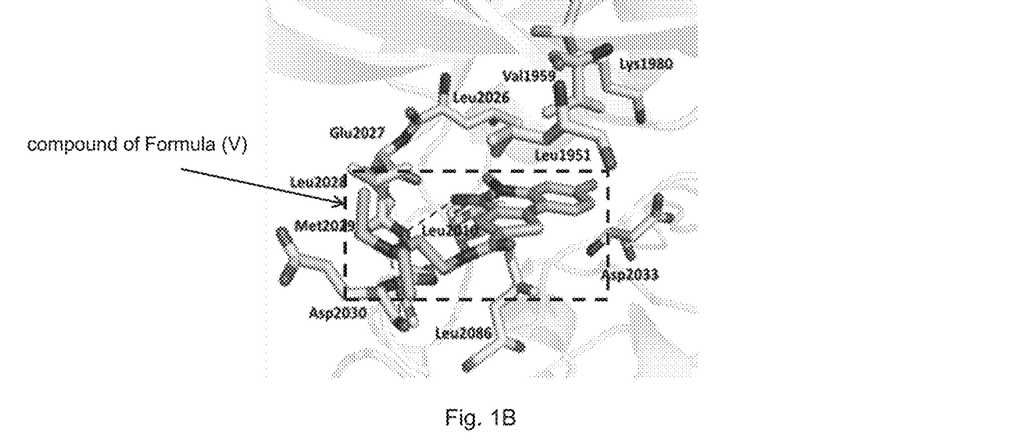
FIG. 1B shows 3D schematic representation of the binding mode between the compound of Formula (V) and the binding pocket of ROS1.

The compound of Formula (V) has been docked into the binding pocket of ROS1 kinase. The docking score of the compound of Formula (V) to ROS1 is −8.464 Kcal/mol. The binding mode of the compound of Formula (V) to ROS1 binding pocket has been further overlapped with that of crizotinib. As shown in FIG. 1A, the hydrophobic aromatic scaffold of the compound of Formula (V) and crizotinib overlapped well, while the hydrophilic "tails" of the compound of Formula (V) was much closer to the hinge when compared to crizotinib. As shown in FIG. 1B, residues on the hinge region including Leu2026, Glu2027, Leu2028, Asp2030 contacted well with the compound of Formula (V). The amino- and carboxyl-moieties of Met2029 both formed hydrogen bonds with the polar atoms of the compound of Formula (V), while the carboxyl of Asp2030 had a hydrogen bond with the tertiary-amine on the "tail". Other residues, such as Leu1951, Val1959, Lys1980, Leu2010, Leu2086, Asp2033 also had hydrophobic interactions with of the compound of Formula (V).

Example 2

In order to prove that the compound of Formula (V) is highly cytotoxic and selective to cancer cells, the cytotoxic effect of the compound of Formula (V) on HCC78 NSCLC cells (with ROS1 rearrangement) and normal lung cells (CCD19-Lu) has been determined.

For MTT assay, 3000 cells were seeded on 96-well plates, then treated with DMSO or various concentrations of the compound of Formula (V) for 72 h. At the end of the incubation, 10 μL of MTT (5 mg/mL; Sigma) was added into each well, and the plates were incubated for an additional 4 hours, then the dark blue crystals were dissolved in 100 μL of the resolved solution (10% SDS and 0.1 mM HCL). Finally, the absorbance was measured by a microplate reader at 570 nm (Tecan, Morrisville, N.C., USA). The cell viability was calculated relative to untreated controls, with results based on at least three independent experiments.

Figure 2A:
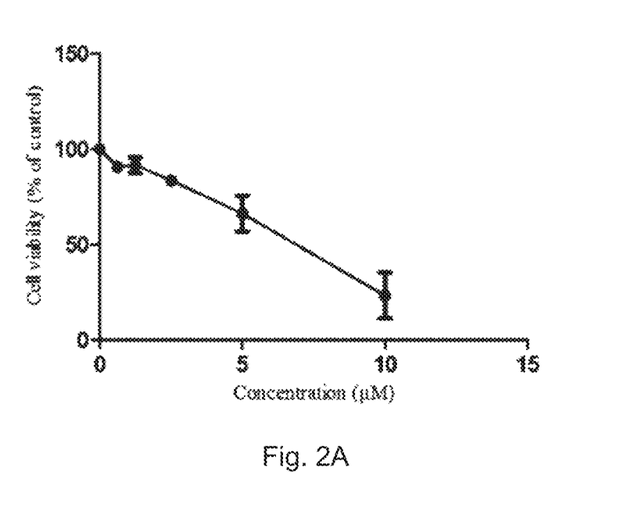
FIG. 2A shows the cell viability relative to untreated controls of HCC78 cells after treatment with the compound of Formula (V) with a concentration of 0-10 μM for 72 h.
Figure 2B:
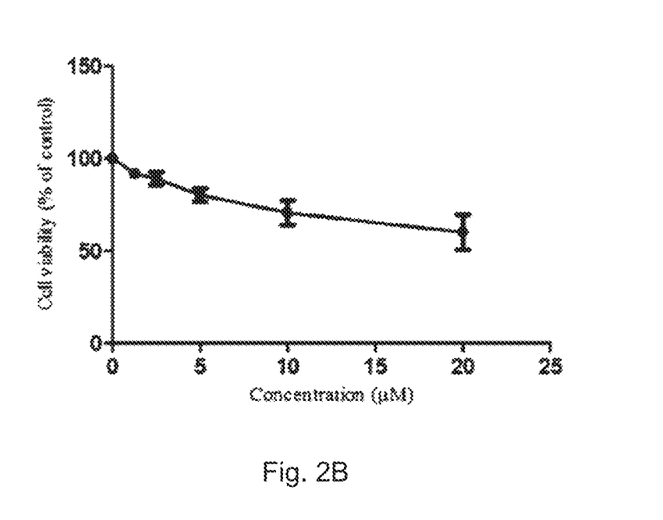
FIG. 2B shows the cell viability relative to untreated controls of lung normal cell CCD19 after treatment with the compound of Formula (V) with a concentration of 0-20 μM for 72 h.
Figure 3A:
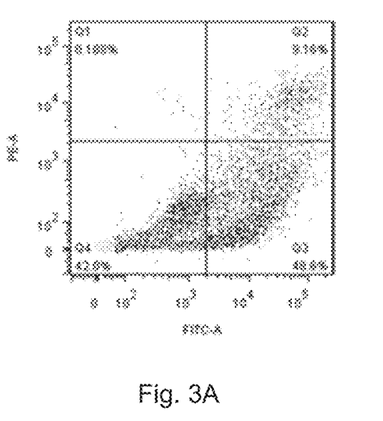
FIGS. 3A, 3B, 3C, 3D, and 3E refer to a Flow Cytometry pattern of HCC78 cells having been treated with different concentrations of the compound of Formula (V) namely with 2.5 μM (FIG. 3C), 5 μM (FIG. 3D) and 10 μM (FIG. 3E) compared with a Flow Cytometry pattern of HCC78 cells having been treated with 2.5 μM crizotinib (FIG. 3A) and a control group (FIG. 3B).
Figure 3B:
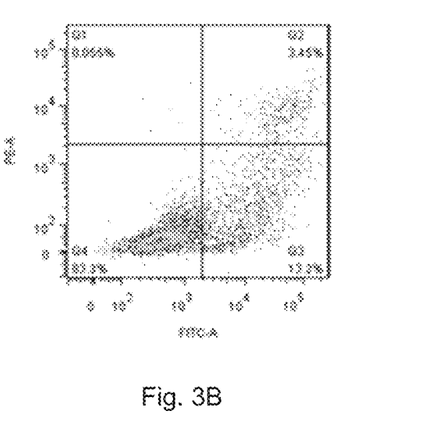
Figure 3C:
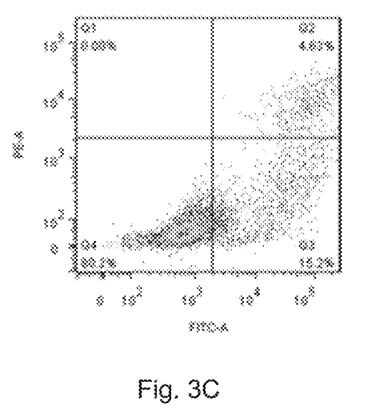
Figure 3D:
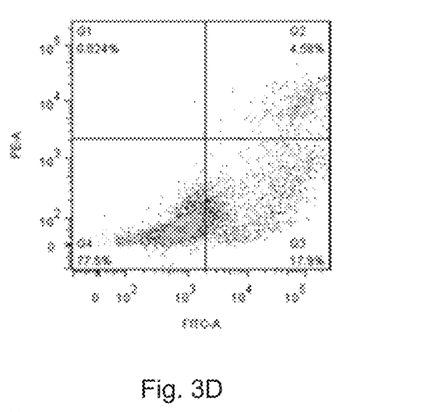
Figure 3E:
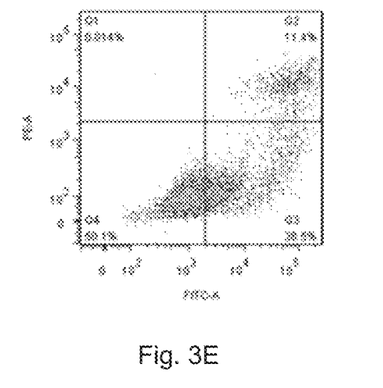
Figure 3F:
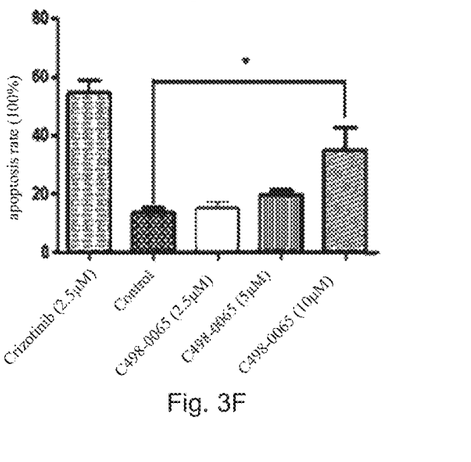
FIG. 3F shows the rate of apoptosis of HCC78 cells having been treated with the compound of Formula (V) (referenced as "C498-0065") with 2.5, 5 or 10 μM, 2.5 μM crizotinib and of the control group.
Figure 4A:
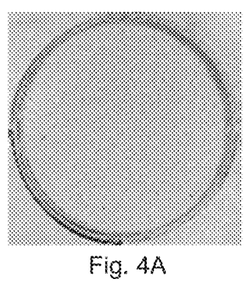
FIGS. 4A, 4B, 4C, 4D, and 4E show the formation of HCC78 cell colonies after treatment with different concentrations of the compound of Formula (V), namely with 1.25 μM (FIG. 4C), 2.5 μM (FIG. 4D) and 5 μM (FIG. 4E) compared with 2.5 μM crizotinib (FIG. 4A) and a control group (FIG. 4B).
Figure 4B:
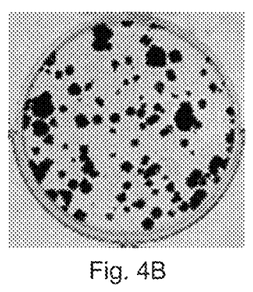
Figure 4C:
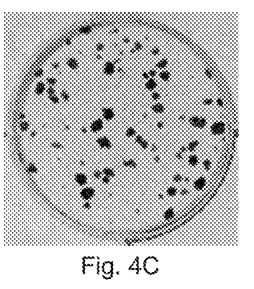
Figure 4D:
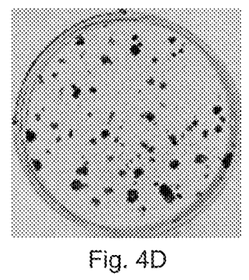
Figure 4E:
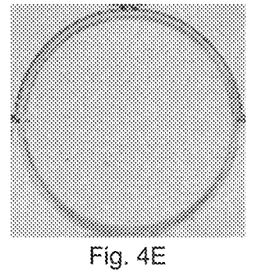
Figure 4F:
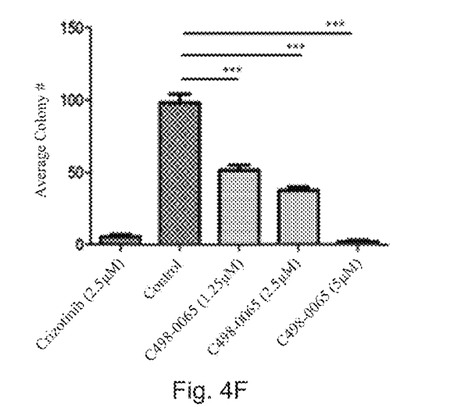
FIG. 4F illustrates the average number of colonies formed in the colony formation assay as shown in FIG. 4A to 4E, i.e. with 1.25 μM, 2.5 μM and 5 μM of compound of Formula (V) (referenced as "C498-0065") compared with 2.5 μM crizotinib and control group.

As evident from FIGS. 2A and 2B, the $IC_{50}$ value of the compound of Formula (V) on HCC78 cells is 6.35±1.44 μM with advantageously lower cytotoxicity on normal lung cells (CCD19-Lu). The $IC_{50}$ in CCD19-Lu is more than 20 μM meaning that the compound of Formula (V) proved to be highly selective towards cancerous cells.

Example 3

Further, to provide additional evidence that the compound of Formula (V) is potent and highly effective in inducing apoptosis in cancer cells, the induced apoptosis in HCC78 cells has been analyzed. HCC78 cells (1.0×10⁵ cells/well) were allowed to attach in a 6-well plates for 24 h, cells were treated with the compound of Formula (V) for 24 h. Subsequently, cells were trypsinized, washed with PBS and stained with 100 μL binding buffer containing 2 μL Annexin-V FITC and 4 μL propidine iodide (PI) incubated in the dark at room temperature for 15 min, before further addition of 400 μL of 1× Annexin-binding buffer. The stained cells were analyzed quantitatively using a Flow Cytometer (BD Biosciences, San Jose, Calif., USA). Data were analyzed by Flow Jo software.

Flow cytometry analysis proved that the compound of Formula (V) exhibits advantageous anti-cancer ability through induction of apoptosis on HCC78 cells, which is exhibited in a concentration-dependent manner. As evident from FIG. 3A to 3F, treatment on HCC78 cells with the compound of Formula (V) induced significant levels of cell apoptosis compared to the control group, which is highly advantageous.

Example 4

Still further, inhibitory effect of the compound of Formula (V) on the colony formation in HCC78 cells has been tested to provide further evidence that the compound of Formula (V) inhibits the formation of colonies of cancerous cell to an exceptional degree, too.

HCC78 cells were seeded on a six-well plate at a density of 500 cells per well. The cells were exposed to various concentrations of the compound of Formula (V). After 10 days, the colonies were fixed with 4% paraformaldehyde and stained with a 0.5% (0.5% w/v) crystal violet solutions, the number of colonies >50 was counted under a dissecting microscope and surviving fractions were calculated.

As shown in FIG. 4A to 4F, colony formation assay demonstrated that the compound of Formula (V) advantageously inhibited the formation of HCC78 cell colonies, which inhibitory effect occurred in a dose-dependent manner.

Example 5

Additionally, the suppression of ROS1 phosphorylation as well as its downstream signaling pathway by the compound of Formula (V) has been studied.

Cells exposed to different concentrations of compound of Formula (V), namely 2.5, 5 and 10 μM or 2.5 μM crizotinib as described above and a control group were washed twice with cold PBS then lysed in RIPA lysis buffer containing protease and phosphatase inhibitors, protein concentration of the cell lysates were measured using the Bio-Rad protein Assay kit (Bio-Rad, Philadelphia, Pa., USA). After equalizing the protein concentrations of the samples, 5× laemmli buffer was added and boiled at 100° C. for 5 min. Equal amounts of protein (20-40 μg per lane) were separated with a 10% SDS-PAGE gel, then the separated proteins were transferred to a nitrocellulose (NC) membrane, which was then exposed to 5% non-fat dry milk in TBS containing 0.1% Tween 20 (0.1% TBST) for 1 hour at room temperature with constant agitation, followed by overnight incubation at 4° C. with primary antibodies, after washing 3 times by TBST, the membranes were incubated with secondary rabbit or mouse fluorescent antibodies, the signal intensity of the membranes was detected by an LI-COR Odessy scanner (Belfast, Me., USA). Antibodies against GAPDH, p-AKT, p-ROS1, ROS1, p-ERK, ERK, p-STAT3, STAT3 were purchased from Cell signaling Technology. Anti-AKT antibody was acquired from Santa Cruz Biotechnology. All primary antibodies were diluted 1:1000, while their recommended secondary antibodies were diluted 1:10000.

Figure 5:
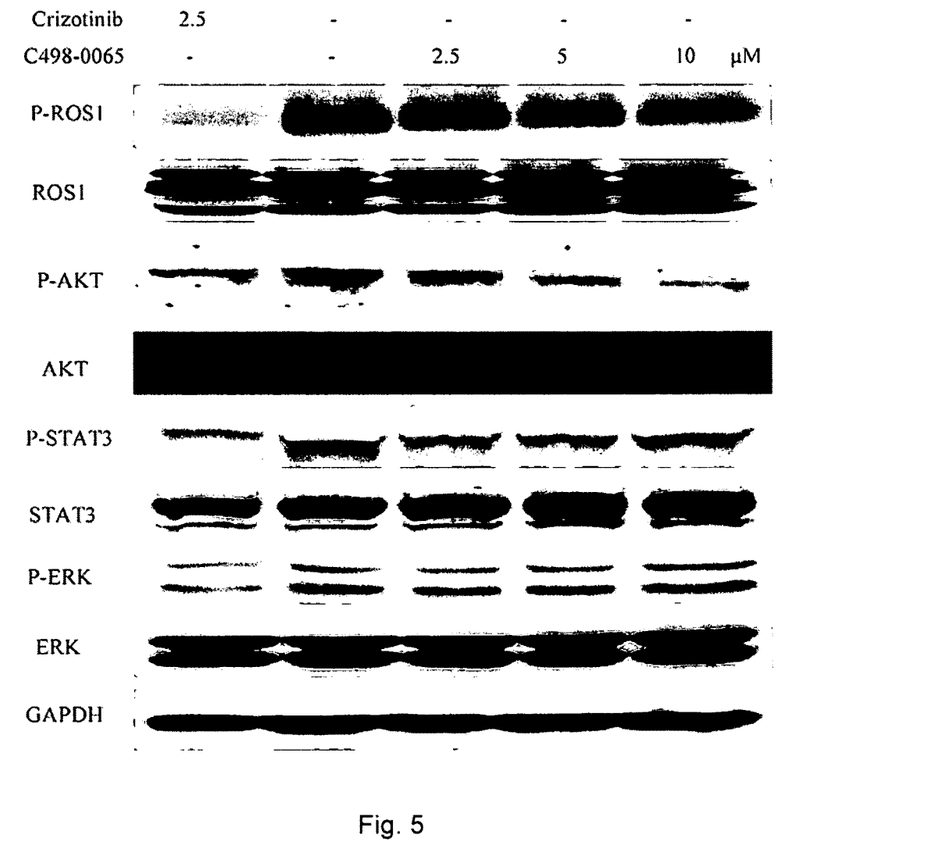
FIG. 5 refers to a western blot and shows the expression of phosphorylated ROS1, ROS1, phosphorylated AKT, AKT, phosphorylated STAT3, STAT3, phosphorylated ERK, ERK and GAPDH of a control group and HCC78 cells treated with 2.5 μM crizotinib, 2.5 μM, 5 μM and 10 μM of compound of Formula (V) (referenced as "C498-0065").

The anti-tumor efficacy of the compound of Formula (V) proved to be correlated with the inhibition of ROS1 phosphorylation and of the ROS1 downstream signaling molecules pERK1/2, pSTAT3 and pAKT as evident from FIG. 5. The effect occurred in a dose-dependent manner. As the analyzed downstream signaling pathway promotes tumor cell survival and proliferation, inhibition of said pathway is suitable to suppress growth and proliferation of cancer cells which, thus, further confirms the exceptional anti-cancer effect of the compound of Formula (V).

The invention claimed is:

1. A method for treating a subject suffering from a disease comprising administering an effective amount of a compound having Formula (III) or a pharmaceutically acceptable salt, solvate or anhydrate thereof to a subject:

Formula (III)

wherein
$R^7$ is a group of Formula (II):

Formula (II)

with n=0 and m=2 and wherein $R^9$ and $R^{10}$ are independent from each other selected from methyl, ethyl or straight chain or branched propyl;

$R^5$ is selected from methyl or ethyl; and three of $R^1$ to $R^4$ are hydrogen and one of them is a halogen selected from Cl, Br or F.

2. The method of claim 1, wherein the disease is cancer.

3. The method of claim 1, wherein the disease is lung cancer.

4. The method of claim 1, wherein the subject is a mammal having an abnormality in ROS1 gene resulting from ROS1 chromosome rearrangement.

5. The method of claim 4, wherein ROS1 chromosome rearrangement is associated with the expression of SCL34A2-ROS1 or CD74-ROS1 fusion kinase.

6. The method of claim 1, wherein the disease is ROS1-dependent non-small-cell lung cancer and wherein the compound has an $IC_{50}$ on non-small-cell lung cancer cells of at most 10 μM and an $IC_{50}$ on normal lung cells being at least 2.5 times higher than the $IC_{50}$ on non-small-cell lung cancer cells.

7. The method of claim 1, wherein the compound is a compound having Formula (IV) or (V) or a pharmaceutically acceptable salt, solvate or anhydrate thereof:

Formula (IV)

Formula (V)

and wherein the disease is ROS1-dependent non-small-cell lung cancer.

8. A method for targeting tumor cells harboring an abnormality in ROS1 gene comprising the step of contacting said cells with a compound of Formula (III) or a salt, solvate or anhydrate thereof:

Formula (III)

wherein
$R^7$ is a group of Formula (II):

Formula (II)

with n=0 and m=2 and wherein $R^9$ and $R^{10}$ are independent from each other selected from methyl, ethyl or straight chain or branched propyl;
$R^5$ is selected from methyl or ethyl; and
three of $R^1$ to $R^4$ are hydrogen and one of them is a halogen selected from Cl, Br or F.

9. The method of claim 8, wherein the proliferation of the tumor cells is inhibited, reduced or prevented or apoptosis of the tumor cells is induced.

10. The method of claim 8, wherein the tumor cells are from a lung tumor.

11. The method of claim 8, wherein the compound of Formula (III) is used in a concentration of at least 2.5 μM.

12. The method of claim 8, wherein the compound is a compound having Formula (IV) or (V)

Formula (IV)

Formula (V)

and wherein the concentration of the compound of Formula (IV) or (V) is at least 5 μM.

13. The method of claim 8, wherein the tumor cells are contacted with the compound for at least 12 h.

14. The method of claim 8, wherein the abnormality in ROS1 gene is a ROS1 chromosome rearrangement.

15. The method of claim 14, wherein the tumor cells express ROS1 fusion kinase selected from SCL34A2-ROS1 or CD74-ROS1 fusion kinase.

16. A pharmaceutical composition comprising a compound of Formula (III)

Formula (III)

wherein
R⁷ is a group of Formula (II):

Formula (II)

with n=0 and m=2 and wherein $R^9$ and $R^{10}$ are independent from each other selected from methyl, ethyl or straight chain or branched propyl;
$R^5$ is selected from methyl or ethyl; and
three of $R^1$ to $R^4$ are hydrogen and one of them is a halogen selected from Cl, Br or F;
or a pharmaceutically acceptable salt, solvate or anhydrate of said compound as active ingredient and further comprising physiologically tolerable excipients.

17. The pharmaceutical formulation of claim 16, wherein the compound is a compound of Formula (IV) or (V)

Formula (IV)

Formula (V)

* * * * *